US006320027B1

(12) United States Patent
Barrett et al.

(10) Patent No.: US 6,320,027 B1
(45) Date of Patent: Nov. 20, 2001

(54) NUCLEOTIDE SEQUENCE OF THE NUCLEOCAPSID GENE OF OROPOUCHE VIRUS

(75) Inventors: Alan D. T. Barrett; Mohammad F. Saeed; Robert B. Tesh; Robert E. Shope, all of Galveston, TX (US); Heiman Wang, Vestavia Hills, FL (US)

(73) Assignee: The Board of Regents of the University of Texas, Austin, TX (US)

(*) Notice: Subject to any disclaimer, the term of this patent is extended or adjusted under 35 U.S.C. 154(b) by 0 days.

(21) Appl. No.: 09/463,005

(22) PCT Filed: Jul. 17, 1998

(86) PCT No.: PCT/US98/14887

§ 371 Date: Jan. 14, 2000

§ 102(e) Date: Jan. 14, 2000

(87) PCT Pub. No.: WO99/03875

PCT Pub. Date: Jan. 28, 1999

Related U.S. Application Data

(60) Provisional application No. 60/052,848, filed on Jul. 17, 1997.

(51) Int. Cl.[7] .......................... C07K 14/175; C07K 16/10

(52) U.S. Cl. .................... 530/350; 530/387.1; 530/391.3

(58) Field of Search ................................ 930/220; 435/4, 435/6; 530/350, 387.1, 391.3

(56) References Cited

PUBLICATIONS

Beaty et al. 1991. Bunyaviridae—Natural History. Current Topics in Microbiology and Immunology 169: 27–78.*

Murphy. 1996. Virus Taxonomy. in Fields, et al., eds. Fundamental Virology, Third Edition. Lippincott–Raven Publishers, Philadelphia. see Table 4 of Chapter 2.*

* cited by examiner

*Primary Examiner*—James Ketter
*Assistant Examiner*—Lisa Gansheroff
(74) *Attorney, Agent, or Firm*—Benjamin Aaron Adler

(57) ABSTRACT

The present invention provides DNA encoding an Oropouche NP protein selected from the group consisting of: (a) isolated DNA which encodes an Oropouche NP protein; (b) isolated DNA which hybridizes to isolated DNA of (a) above and which encodes an Oropouche NP protein; and (c) isolated DNA differing from the isolated DNAs of (a) and (b) above in codon sequence due to the degeneracy of the genetic code, and which encodes an Oropouche NP protein. Also provided is a kit for the immunodetection of Oropouche virus.

3 Claims, 19 Drawing Sheets

AGTAGTGTAC TCCACTATTC AAAACATAAA AAGAAATTCC
AATAATGTCA GAGTTCATTT TCAACGATGT ACCACAACGG
ACTACATCTA CATTTGATCC GGAAGCAGCA TATGTGGCAT
TTGAAGCTAG ATACGGACAA GTGCTCAATG CTGGTGTTGT
TAGAGTCTTC TTCCTCAACC AAAAGAAGGC CAAAGATGTC
TTACGTAAGA CATCGAGGCC CATGGTTGAC CTTACTTTTG
GTGGGGTCCA ATTTGCAATG GTTAATAACC ATTTCCCACA
GTTCCAATCG AATCCAGTGC CGGACAACGG TCTTACCTTG
CACCGTCTGT CAGGATACCT AGCGCGCTGG GCCTTTACTC
AGATGCGATC ACCAATTAAG CAAGCTGAGT TCAGAGCTAC
TGTAGTAGTG CCTTTGGCTG AGGTAAAAGG CTGTACTTGG
AATGATGGTG ATGCAATGTA CCTGGGGTTT GCTGCTGGTG
CTGAGATGTT CCTGCAGACG TTCACTTTCT TCCCTTTGGT
GATTGAGATG CATAGGGTTC TCAAGGATGG CATGGATGTC
AACTTTATGA AGAAAGTCCT CCGGCAACGG TATGGCCAAA
AAACTGCCGA GCAATGGATG CGTGAAGAAA TAGTTGCTGT
AAGAGCAGCT TTTGAAGCTG TAGGCACTCT GGCCTGGGCC
AGAACTGGAT TCTCCCCAGC AGCAAGAGAC TTCTTGCGCC
AATTCGGAAT TGGCATATAG TGGAGTACAC TACT (SEQ ID NO:3)

Fig. 2

(SEQ ID NO:4) 3'----GTATTTTTCTTTAAGGTTATTACAGTCACAAGTAAA----5'
5'-AAAGAGGATCCAATAATGTCAGAGTTCATTT-3' (SEQ ID NO:5)

(ORON5)

(ORON3)

(SEQ ID NO:6) 3'-TTAAGCCTTAACCGTATATCACCTTAAGTG-5'
5'----CCAATTCGGAATTGGCATATAGTGGAGTACACTACT----3' (SEQ ID NO:7)

Fig. 4A

ATAAATAAGG GAGTTAAACA TGGGGGGTTC TCATCATCAT

I R E L N M G G S H H H

CATCATCATG GTATGGCTAG CATGACTGGT GGACAGCAAA

H H H G M A S M T G G Q Q

TGGGTCGGGA TCTGTACGAC GATGACGATA AGGATCCAAT

M G R D L Y D D D D K D P I

AATGTCAGAG TTCATTTTCA ATGATGTACC ACAACGGACT

M S E F I F N D V P Q R T

ACATCTACAT TTGATCCGG (SEQ ID #8)

T S T F D P (SEQ ID #9)

Fig. 7

```
                                                                         NS_s
         10        20        30        40        50        60        70
         |         |         |         |         |         |         |
AGTAGTGTACTCCACTATTCAAAACATAAAAAGAAATTCCAATAATGTCAGAGTTCATTTCAACGATGTAC
                                              M  S  E  P  I  F  N  D  V
                                              NP →                    M  Y

         80        90       100       110       120       130       140
         |         |         |         |         |         |         |
CACAACGGACTACACTCTACATTTGATCCGGAAGCAGCATATGTGGCATTTGAAGCTAGATACGGACAAGTGC
 H  N  G  L  H  L  H  L  I  R  K  Q  H  M  W  H  L  K  L  D  T  D  K  C
 P  Q  R  T  T  S  T  F  D  P  E  A  A  Y  V  A  F  E  A  R  Y  G  Q  V

        150       160       170       180       190       200       210
         |         |         |         |         |         |         |
TCAATGCTGGTGTTGTTAGAGTCTTCTTCCTCAACCAAAAGAAGGCCAAAGATGTCTTACGTAAGACATCGA
 S  M  L  V  L  L  E  S  S  S  S  T  K  R  R  P  K  M  S  Y  V  R  H  R
 L  N  A  G  V  V  R  V  F  F  L  N  Q  K  K  A  K  D  V  L  R  K  T  S
```

```
220        230        240        250        260        270        280
 |          |          |          |          |          |          |
GGCCCATGGTTGACCTTACTTTTGGTGGGGTCCAATTTGCAATGGTTAATAACCATTTCCCACAGTTCCAAT
 G  P  W  L  T  L  L  L  V  G  S  N  L  Q  W  L  I  T  I  S  H  S  S  N
R  P  M  V  D  L  T  F  G  G  V  Q  F  A  M  V  N  N  H  F  P  Q  F  Q

290       300        310        320        330        340        350        360
 |         |          |          |          |          |          |          |
CGAATCCAGTGCCGGACAACGGTCTTACCTTGCACCGTCTGTCAGGATACCTAGCGCGCTGGGCCTTTACTC
 R  I  Q  C  R  T  T  V  L  P  C  T  V  C  Q  D  T  (SEQ ID NO:12)
S  N  P  V  P  D  N  G  L  T  L  H  R  L  S  G  Y  L  A  R  W  A  F  T

      370        380        390        400        410        420        430
       |          |          |          |          |          |          |
AGATGCGATCACCAATTAAGCAAGCTGAGTTCAGAGCTACTGTAGTAGTGCCTTTGGCTGAGGTAAAAGGCT

Q  M  R  S  P  I  K  Q  A  E  F  R  A  T  V  V  V  P  L  A  E  V  K  G
```

```
  440        450        460        470        480        490        500
    |          |          |          |          |          |          |
GTACTTGGAATGATGGTGATGCAATGTACCTGGGGTTTGCTGCTGGTGCTGAGATGTTCCTGCAGACGTTCA

C  T  W  N  D  G  D  A  M  Y  L  G  F  A  A  G  A  E  M  F  L  Q  T  F

 510        520        530        540        550        560        570
   |          |          |          |          |          |          |
CTTTCTTCCCTTTGGTGATTGAGATGCATAGGGTTCTCAAGGATGGCATGGATGTCAACTTTATGAAGAAAG

T  F  F  P  L  V  I  E  M  H  R  V  L  K  D  G  M  D  V  N  F  M  K  K

580        590        600        610        620        630        640
  |          |          |          |          |          |          |
TCCTCCGGCAACGGTATGGCCAAAAAACTGCCGAGCAATGGATGCGTGAAGAAATAGTTGCTGTAAGAGCAG

V  L  R  Q  R  Y  G  Q  K  T  A  E  Q  W  M  R  E  E  I  V  A  V  R  A
```

```
650       660        670        680        690        700        710        720
 |         |          |          |          |          |          |          |
CTTTTGAAGCTGTAGGCACTCTGGCCTGGGCCAGAACTGGATTCTCCCCAGCAGCAAGAGACTTCTTGCGCC

A  F  E  A  V  G  T  L  A  W  A  R  T  G  F  S  P  A  A  R  D  F  L  R

       730        740        750
        |          |          |
AATTCGGAATTGGCATATAGTGGAGTACACTACT  (SEQ ID NO:3)

Q  F  G  I  G  I  (SEQ ID NO:11)
```

Fig. 11D

NUCLEOTIDE SEQUENCE OF THE NUCLEOCAPSID GENE OF OROPOUCHE VIRUS

CROSS-REFERENCE TO RELATED APPLICATION

This patent application claims benefit of provisional patent application U.S. Ser. No. 60/052,848, filed Jul. 17, 1997, now abandoned.

BACKGROUND OF THE INVENTION

1. Field of the Invention

The present invention relates generally to the fields of molecular immunology and virology. More specifically, the present invention relates to nucleotide sequence of the nucleocapsid gene of oropouche virus.

2. Description of the Related Art

Oropouche (ORO) virus, the causative agent of oropouche fever, has emerged during the past 30 years as an increasing health problem in tropical regions of South and Central America. Since 1961 a number of epidemics of oropouche fever have been recorded involving several thousand people. Oropouche fever in humans is characterized by abrupt onset of fever, chills, severe headache, generalized myalgia, arthralgia, anorexia, nausea, vomiting, weakness, dizziness, and photophobia. Because of the non-specific nature of symptoms and paucity of diagnostic virus laboratories in the oropouche-endemic region, the disease often is either unrecognized or misdiagnosed as being an infection caused by dengue or other similar viruses.

The oropouche virus belongs to the genus Bunyavirus of family Bunyaviridae. Based on antigenic characteristics, the bunyavirus genus has been divided into 18 serogroups and oropouche virus is one of 25 viruses that have been placed in Simbu serogroup. The genome of oropouche virus consists of three segments of single stranded, negative sense RNA designated as Large (L), Medium (M) and Small (S) RNAs. The L RNA encodes the L (RNA polymerase) protein; the M RNA encodes two glycoproteins G1 and G2 and a nonstructural protein NSm; and the S RNA encode nucleocapsid (NP) protein and a non-structural (NSs) protein.

To date, the molecular biology of bunyaviruses has focused on a small number of viruses and very little information is available on other viruses, especially the Simbu serogroup viruses. The S RNA has been sequenced for several members of Bunyamwera and California encephalitis serogroups but only Tinaroo, Akabane and Aino viruses have been sequenced for the Simbu serogroup.

Current techniques for the identification and diagnosis of Oropouche infection include neutralization test, hemaglutination inhibition and complement fixation to detect anti-oropouche antibodies. ELISA using antigen produced from infectious virus has also been used but production of antigen is expensive, hazardous and highly variable from batch to batch. This ELISA also gives too many "false positives".

The prior art is deficient in the lack of knowledge of many aspects of the molecular biological properties of oropouche virus, including the nucleotide sequence of the nucleocapsid gene of oropouche virus. The present invention fulfills this long-standing need and desire in the art.

SUMMARY OF THE INVENTION

The S RNA of the Oropouche virus was cloned and sequenced. The sequence analysis of the S RNA revealed that oropouche virus is related to, but genetically distinct from the Simbu serogroup viruses. The total length of the S-RNA was found to be 754 nucleotides and two overlapping open reading frames (ORFs) of 693 and 273 nucleotides were identified which encoded the NP and NSs proteins, respectively.

In addition, the NP protein was also cloned and expressed in an *E.coli* expression system. SDS-PAGE and Western blotting analysis revealed that the molecular weight of the recombinant protein is the same as that of the viral NP and that it was recognized by oropouche-specific antisera. Reactivity pattern of the recombinant protein with sera raised against 15 other Simbu serogroup viruses was indistinguishable from the reactivity pattern of the authentic viral NP. Furthermore, like the viral NP, the recombinant protein failed to react with sera raised against dengue viruses 1 & 2 and 4 bunyaviruses belonging to other serogroups. Thus, based on these data, the recombinant NP protein can be an important diagnostic tool for the identification of Oropouche infection which would be safer, less expensive and easier to produce in large quantities.

It is an object of the present invention to provide the Oropouche NP gene sequence which can be used to design oligonucleotide primers for reverse transcriptase-PCR to amplify Oropouche viral RNA from virus-infected cell cultures and serum samples.

It is also another object of the present invention to express Oropouche virus NP gene in *E. coli*.

It is another object of the present invention to provide Oropouche virus NP protein useful in detecting anti-NP antibodies so as to be able to diagnose Oropouche virus infection and seroprevalence.

In one embodiment of the present invention, there is provided DNA encoding a Oropouche NP protein selected from the group consisting of: (a) isolated DNA which encodes a Oropouche NP protein; (b) isolated DNA which hybridizes to isolated viral RNA or complementary DNA of (a) above and which encodes a Oropouche NP protein; and (c) isolated DNA differing from the isolated DNAs of (a) and (b) above in codon sequence due to the degeneracy of the genetic code, and which encodes a Oropouche NP protein.

In another embodiment of the present invention, there is provided a vector capable of expressing the DNA of the present invention adapted for expression in a recombinant cell and regulatory elements necessary for expression of the DNA in the cell.

In yet another embodiment of the present invention, there is provided an isolated and purified Oropouche NP protein encoded by DNA selected from the group consisting of: (a) isolated DNA which encodes a Oropouche NP protein; (b) isolated DNA which hybridizes to isolated DNA of (a) above and which encodes a Oropouche NP protein; and (c) isolated DNA differing from the isolated DNAs of (a) and (b) above in codon sequence due to the degeneracy of the genetic code, and which encodes a Oropouche NP protein.

In still yet another embodiment of the present invention, there is provided a kit for the immunodetection of Oropouche virus DNA or RNA.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows the nucleotide sequence of S RNA cDNA (SEQ ID No: 3). The cDNA was sequenced in both directions using sense and antisense primers. Only the sense strand is shown.

FIGS. 4A–4B show the amplification of the NP gene. FIG. 4A shows the nucleotide sequence of oropoucheN5 (upstream, SEQ ID NOs: 4 and 5) and oropoucheN3 (downstream, SEQ ID NOs: 6 and 7) primers. Binding of the primers to the complementary sequence on S cDNA is shown. Nucleotides that are changed to create BamH1 (upstream primer) and EcoRI (downstream primer) sites are underlined. FIG. 4B shows the PCR product analyzed by electrophoresis. M: Molecular wt. markers (O X174 HaeIII digested DNA); lane 1: reaction containing S cDNA; lane 2: reaction containing no DNA.

FIG. 5A shows the expression vector (pTrcHisB) showing promoter region, translation start site (ATG), site for histidine tag (His6), enterokinase cleavage site, multiple cloning site (MCS) and transcription termination site (term). FIG. 5B shows gel electrophoresis of digested plasmid DNAs.

FIG. 7 shows the nucleotide sequence of the recombinant plasmid. Only partial sequence is shown to indicate in frame cloning of NP cDNA (highlighted).

FIG. 10A shows the result from SDS-polyacrylamide gel electrophoresis. FIG. 10B shows the result from Western blotting using oropouche-specific mouse antiserum. Lane 1, protein extract before purification; lane 2, fraction from 50 mM immidazole elution; lanes 3–5, fractions from 200 mM immidazole elution; lanes 6 and 7, fractions from 500 mM immidazole elution.

FIGS. 11A–11D show the deduced amino acid sequence of the Oropouche NP protein (SEQ ID NO: 11) and NSs protein (SEQ ID NO: 12).

DETAILED DESCRIPTION OF THE INVENTION

Figure 1:
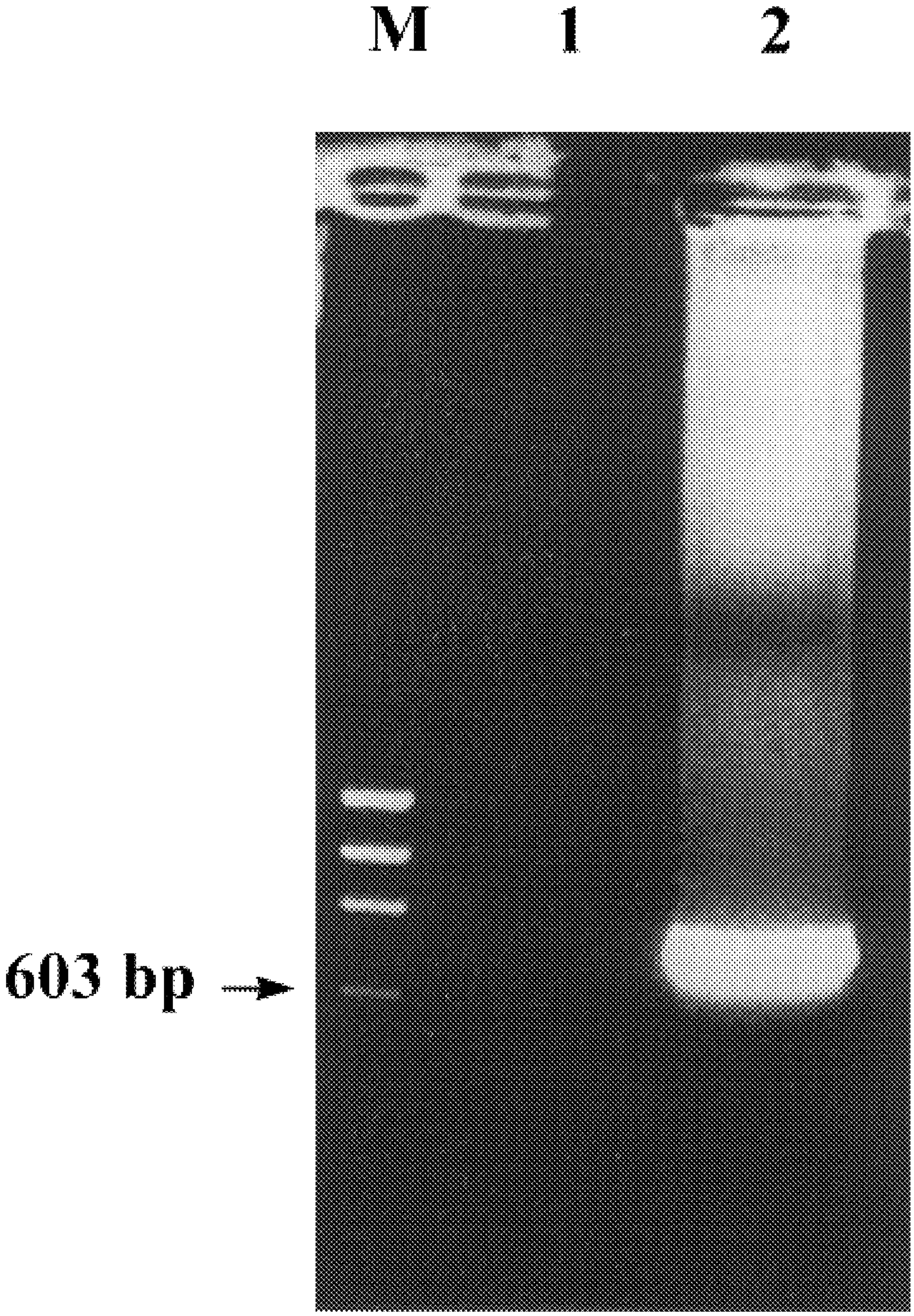
FIG. 1 shows the synthesis of cDNA from S RNA by RT-PCR. M: molecular wt. marker (O X174 HaeIII digested DNA); Lane 1: Negative control (no viral RNA); lane 2: RNA from oropouche virus infected supernatant.

As used herein, the term “cDNA” shall refer to the DNA copy of the mRNA transcript of a gene.

By “substantially pure DNA” is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein.

As used herein, the term “derived amino acid sequence” shall mean the amino acid sequence determined by reading the triplet sequence of nucleotide bases in the cDNA.

As used herein, the term “PCR” refers to the polymerase chain reaction that is the subject of U.S. Pat. Nos. 4,683,195 and 4,683,202 to Mullis, and other improvements now known in the art.

A “replicon” is any genetic element (e.g., plasmid, chromosome, virus) that functions as an automous unit of DNA replication in vivo; i.e., capable of replication under its own control.

A “vector” is a replicon, such as plasmid, phage or cosmid, to which another DNA segment may be attached so as to bring about the replication of the attached segment.

An “origin of replication” refers to those DNA sequences that participate in DNA synthesis.

A DNA “coding sequence” is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, virus sequences, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

An “expression control sequence” is a DNA sequence that controls and regulates the transcription and translation of another DNA sequence. A coding sequence is “under the control” of transcriptional and translational control sequences in a cell when RNA polymerase transcribes the coding sequence into mRNA, which is then translated into the protein encoded by the coding sequence.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$ $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-galactosidase, urease, glucose oxidase plus peroxidase and alkaline phosphatase. U.S. Pat. Nos. 3,654,090, 3,850, 752, and 4,016,043 are referred to by way of example for their disclosure of alternate labeling material and methods.

As used herein, the term "host" is meant to include not only prokaryotes but also eukaryotes such as yeast, plant and animal cells. A recombinant DNA molecule or gene which encodes a Oropouche NP protein of the present invention can be used to transform a host using any of the techniques commonly known to those of ordinary skill in the art. Especially preferred is the use of a vector containing coding sequences for the gene which encodes a human or non-human Oropouche NP protein of the present invention for purposes of prokaryote transformation.

Prokaryotic hosts may include *E coli, S. tymphimurium, Serratia marcescens*, Mycobacterium and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The present invention is directed to DNA or RNA encoding a Oropouche NP protein selected from the group consisting of: (a) isolated DNA which encodes an Oropouche NP protein; (b) isolated DNA which hybridizes to isolated DNA of (a) above and which encodes an Oropouche NP protein; and (c) isolated DNA differing from the isolated DNAs of (a) and (b) above in codon sequence due to the degeneracy of the genetic code, and which encodes a Oropouche NP protein. Preferably, the DNA has the sequence shown in SEQ ID No. 3. More preferably, the DNA encodes a Oropouche NP protein having the amino acid sequence shown in SEQ ID No. 11.

The present invention is also directed to a vector capable of expressing the DNA of the present invention adapted for expression in a recombinant cell and regulatory elements necessary for expression of the DNA in the cell. Preferably, the vector contains DNA encoding a Oropouche NP protein having the amino acid sequence shown in SEQ ID No. 11.

The present invention is also directed to a host cell transfected with the vector described herein, said vector expressing a Oropouche NP protein. Representative host cells include consisting of bacterial cells, mammalian cells and insect cells.

The present invention is also directed to a isolated and purified Oropouche NP protein coded for by DNA selected from the group consisting of: (a) isolated DNA which encodes a Oropouche NP protein; (b) isolated DNA which hybridizes to isolated DNA of (a) above and which encodes a Oropouche NP protein; and (c) isolated DNA differing from the isolated DNAs of (a) and (b) above in codon sequence due to the degeneracy of the genetic code, and which encodes a Oropouche NP protein. Preferably, the isolated and purified Oropouche NP protein having the amino acid sequence shown in SEQ ID No. 11.

The present invention is also directed to a method of detecting expression of the protein of the present invention, comprising the steps of: (a) contacting mRNA obtained from the cell with the labeled hybridization probe; and (b) detecting hybridization of the probe with the mRNA.

The present invention is further directed to a kit for use in molecular biological tests to identify individuals infected with Oropouche virus. It is contemplated that anti-Oropouche NP protein antibodies may be employed to detect the Oropouche virus. Kits are provided for use in the immunodetection of Oropouche virus, and include kits for clinical diagnosis and kits for use in antigen or antibody purification or titering, as appropriate. More specifically, a preferred kit in accordance with the present invention will contain a recombinant Oropouche NP protein; anti-Oropouche antibodies; and a conjugated secondary antibody. Using the teachings of the instant specification, a person having ordinary skill in this art would be able to prepare vaccine for use against the oropouche virus.

The following examples are given for the purpose of illustrating various embodiments of the invention and are not meant to limit the present invention in any fashion.

EXAMPLE 1

Synthesis of S RNA cDNA

Vero cells were infected with Oropouche virus for 3 days and cell free supernatant was collected. To extract viral RNA, the supernatant (1 ml) was treated with proteinase K and SDS for 1 hour, followed by phenol-choloroform extraction and ethanol precipitation. Subsequently, the RNA was dissolved in 5 $\mu$l of RNase free deionized water. Reverse transcription was carried out in a mixture containing sense primer (5'-AGTAGTGTACTCCACTAT-3') (SEQ ID No: 1), RT buffer, dNTPs, RNasin and 0.5 U RAV-2, RT at 55° C. for 2 hours. For PCR, antisense primer (5'-AGTAGTGTGGCTCCACAT-3) (SEQ ID No: 2), PCR buffer and 0.6 U Taq Polymerase were added and 30 cycles of denaturation (95° C., 40 sec.), annealing (52° C., 40 sec.) and elongation (72° C., 4 minutes) were carried out. The product was analyzed by electrophoresis on a 1.2% agarose gel containing ethidium bromide, and visualized under UV-light (FIG. 1).

EXAMPLE 2

Sequencing

S RNA cDNA was further sequenced in both directions using sense and antisense primers (FIG. 2). The total length of the S-RNA was found to be 754 nucleotides (SEQ ID No: 3) and two overlapping open reading frames (ORFs) of 693 and 273 nucleotides were identified which encoded the NP and NSs proteins, respectively (FIGS. 11A–11D).

EXAMPLE 3

Genetic Analysis of ORO Virus Strains

The N-coding region of 13 strains of oropouche virus was amplified by RT-PCR, followed by direct sequencing of the amplified product. The nucleotide sequences were aligned using the Clustal program in the PC gene package and dendrogram was generated.

Figure 3:
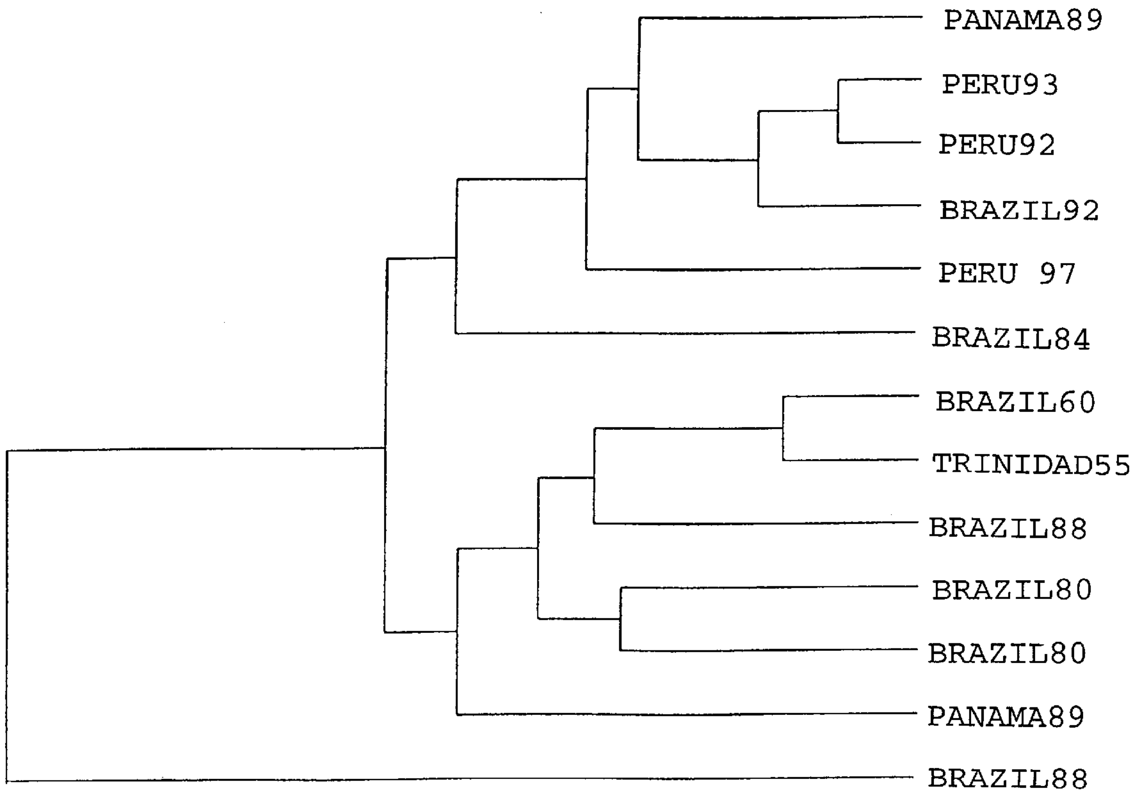
FIG. 3 shows genetic analysis of oropouche virus strains.

The N-protein gene of 13 strains of oropouche virus has been compared (FIG. 3) and indicates there are at least two independent genetic lineages of oropouche virus. Although the strains could be distinguished genetically, serological tests using neutralization assays indicated that strains of oropouche virus were not antigenically distinct (Table 1). Table 2 shows a description of the oropouche strains described in Table 1.

The prototype oropouche strain (Trinidad55) and a representative strain from each lineage (Peru93 from lineage I, Brazil80 from lineage II, and Brazil88 from lineage III) were selected for the assay. Approximately 100 plaque forming units (pfu) were mixed with various dilutions of anti-Trrinidad55 or anti-Peru93 MIAF and incubated for 30 minutes at 37° C. Subsequently, the virus-antibody mixture was mixed with cell culture medium containing 2% fetal bovine serum and 1% agarose, and plated on a confluent mono-layer of Vero cells in a six well plate. Plates were then incubated at 37° C. for 4 days. After the incubation period monolayers were stained with Neutral Red solution and plaques were counted 12–16 h later. Neutralization titers, shown in the table, were calculated as the dilution of MIAF required to inhibit 50% of pfu. A less than four-fold difference in the neutralization titer of MIAFs between different strains tested indicates no significant antigenic difference in the viral surface glycoproteins and hence between strains.

TABLE 1

| Neutralization of ORO Virus Isolates by Mouse Polyclonal Immune Ascitic Fluids | | |
|---|---|---|
| | Mouse Immune Ascitic Fluid | |
| Virus | anti-Trinidad55 | anti-Peru93 |
| Tinidad55 | 2560* | NT |
| Peru93 | NT | 5120 |
| Brazil80 | 2560 | 2560 |
| Brazil89 | 5120 | 5120 |

NT: not tested;
*numbers refer to the neutralization titers expressed as the dilution of mouse hyperimmune ascitic fluid required to inhibit 50% of plaque forming units in test.

TABLE 2

Locations, Years, and Sources of Isolation of ORO Virus Strains

| Strain | Country | State | Community | Year | Source | abbreviation* |
|---|---|---|---|---|---|---|
| TRVL 9760 | Trinidad | | Sangre Grande | 1955 | Human | Trinidad55 |
| BeAn 19991 | Brazil | Para | Santa Maria | 1960 | *B. tridactylus* | Brazil60 |
| BeH 379693 | Brazil | Para | Castanhal | 1980 | Human | Brazil80 |
| BeH 390233 | Brazil | Amazonas | Manaus | 1980 | Human | Brazil80 |
| BeAn 423380 | Brazil | Para | Tucurui | 1984 | *Nasau nasau* | Brazil84 |
| BeH 473358 | Brazil | Maranhao | Pto. Franca | 1988 | *C. paraensis* | Brazil88 |
| BeH 475248 | Brazil | Para | Tucurui | 1988 | Human | Brazil88 |
| BeH 505442 | Brazil | Rondonia | Ariquemes | 1992 | Human | Brazil92 |
| IQT 1690 | Peru | | Iquitos | 1992 | Human | Peru92 |
| MD 023 | Peru | | Madre de Dios | 1993 | Human | Peru93 |
| IQT 4083 | Peru | | Iquitos | 1997 | Human | Peru97 |
| GML444477 | Panama | | Chame | 1989 | Human | Panama89 |
| GML44491 | Panama | | Chame | 1989 | Human | Panama89 |

*Abbreviation refers to that used in phylogenetic tree

Nucleotide sequences for the small RNA of three other members of the Simbu serogroup, Akabane (AKA) and Tinaroo (TIN), have been published by Akashi et al., (J. Gen. Virol. 78: 2847–2851 (1997)) and Aino by Akashi et al., (Viral Research 1: 51–63 (1984)). Table 3 shows a comparison of the nucleotide and amino acid sequences for the N-protein gene of TIN, AKA, ORO, and the first published Simbu serogroup sequence of Aino virus. As can be seen, all four viruses are distinct viruses although TIN and AKA viruses are closely related to each other.

TABLE 3

| Comparison Between ORO and Other Simbu Serogroup Viruses | | | | | |
|---|---|---|---|---|---|
| | | Amino Acid Identity in N Protein (%) | | | |
| | | ORO | TIN | AKA | AINO |
| Nucleotide identity | ORO | — | 692 | 68.8 | 69.2 |
| in S RNA* (%) | TIN | 71.2 | — | 98.8 | 81.5 |
| | AKA | 70.9 | 95.2 | — | 82.4 |
| | AINO | 69.4 | 77.7 | 77.3 | — |

*Nucleotide identity excluding the 5' NCR.

EXAMPLE 4

Amplification of the ORO NP Gene

Figure 4B:
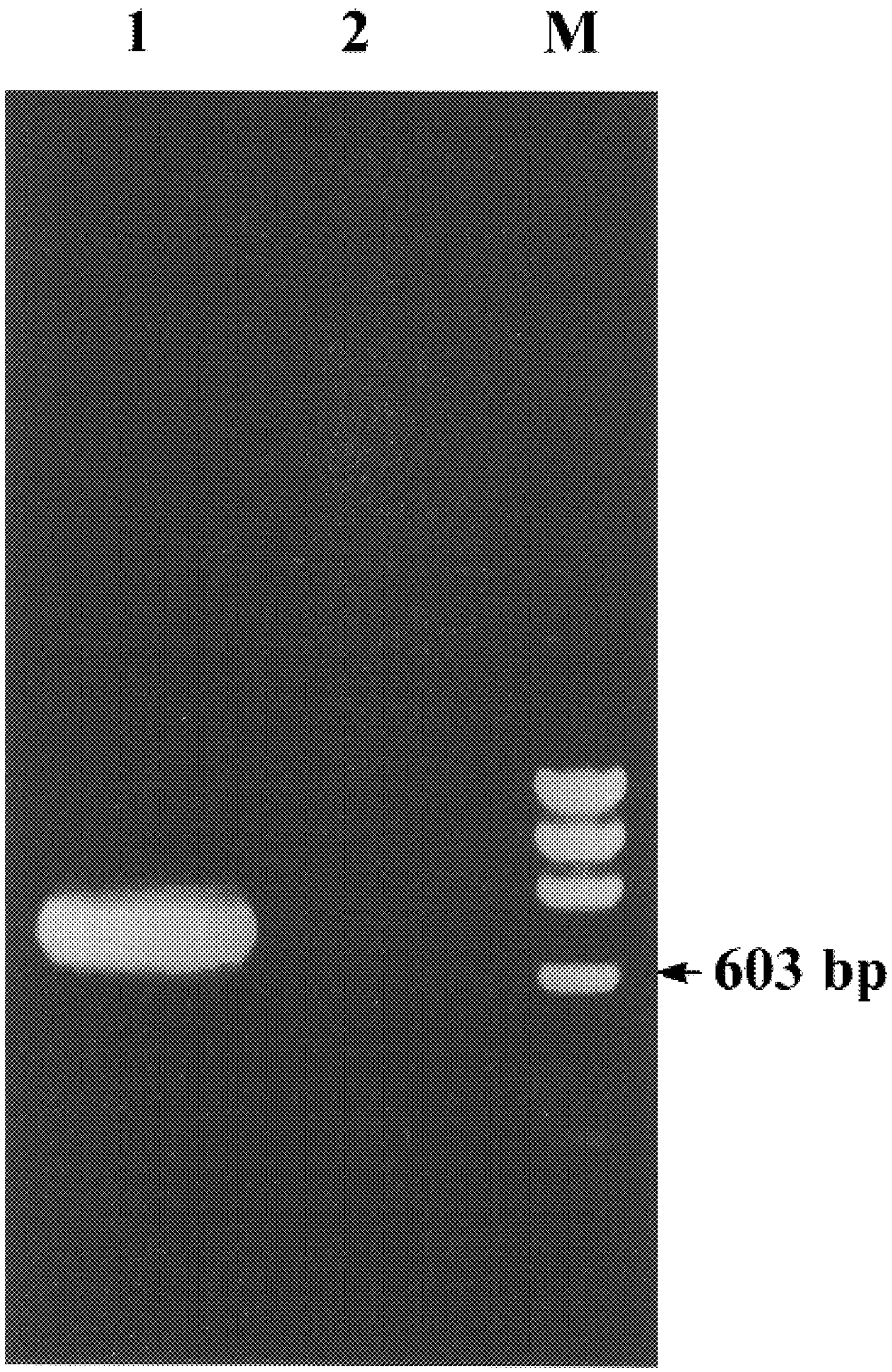

To amplify the NP gene, S cDNA was mixed with both upstream and downstream primers (500 ng each), dNTPs, PCR buffer and Taq DNA polymerase. The nucleotide sequence of oropouche N5 (upstream, SEQ ID NOs: 4 and 5) and oropouche N3 (downstream, SEQ ID NOs: 6 and 7) primers are shown in FIG. 4A. Nucleotides that are changed to create BamH1 (upstream primer) and EcoRI (downstream primer) sites are underlined. Reaction was carried out for 30 cycles, each consisting of denaturation (95° C., 40 sec.), annealing (60° C., 40 sec.) and elongation (72° C., 4 min.) steps. The product was analyzed by electrophoresis through a 1.2% agarose gel containing ethidium bromide and visualized under UV-light (FIG. 4B).

EXAMPLE 5

Cloning of the ORO NP Gene

Figure 5A:
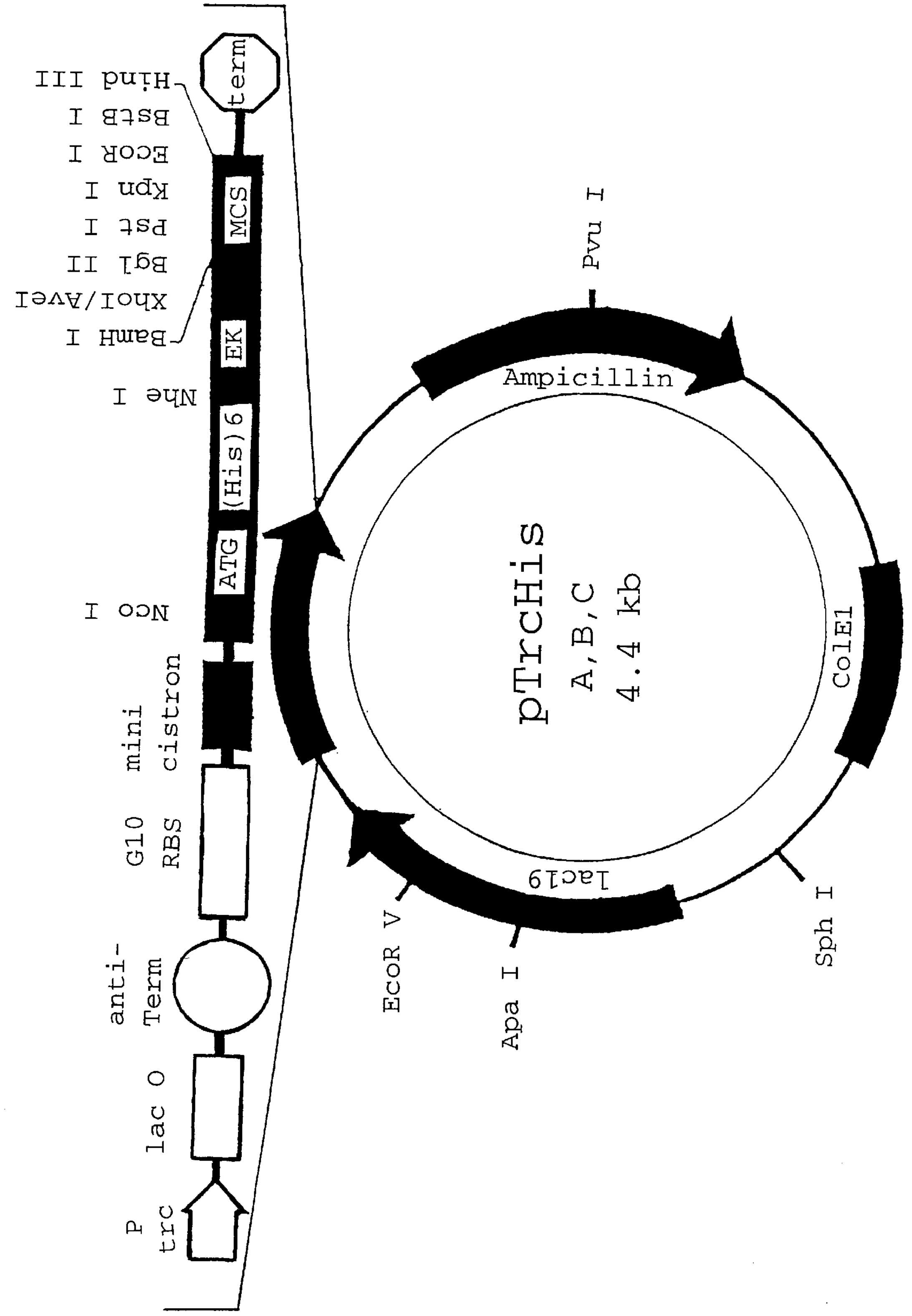
FIGS. 5A–5B show the cloning of NP gene into the expression vector.
Figure 5B:
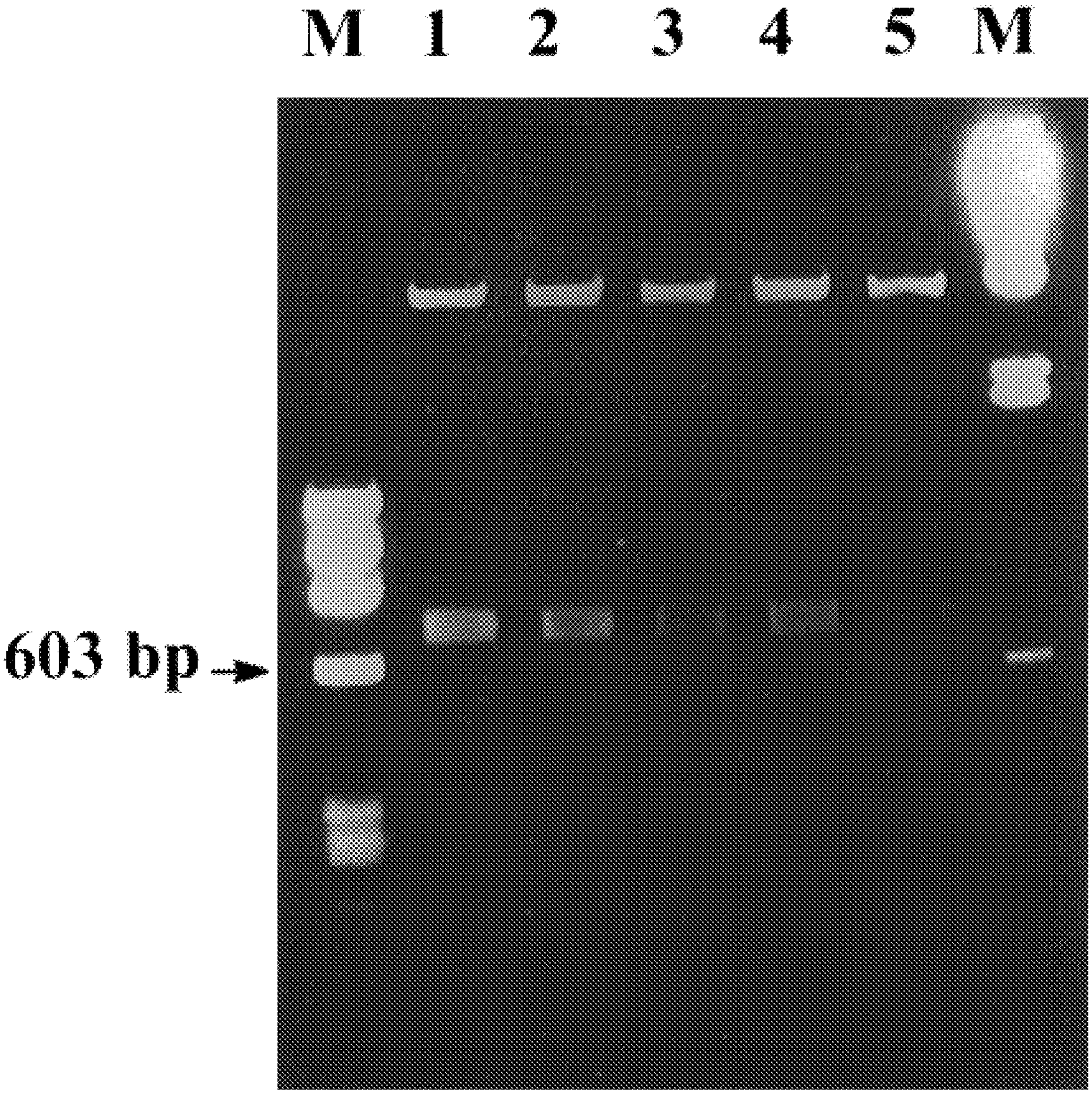

To clone the NP gene, expression vector pTrcHisB (FIG. 5A) was used. The NP cDNA was digested with BamH1 and EcoRI and then ligated to BamH1 and EcoRI digested pTrcHisB vector, using phage T4 DNA ligase. Ligation was carried out at 14° C. overnight. Ligation mixture was then used to transform *E.coli* TOP10 by heat shock in calcium chloride buffer. Transformants were selected on LB-agar plates containing ampicillin (50 μg/ml). Subsequently, 5 colonies were picked, grown in LB broth and plasmid DNAs were isolated which were then linearized using EcoR1 enzyme. Digested plasmid DNAs were electrophoresed through a 0.8% agarose gel containing ethidium bromide and visualized under UV-light.

EXAMPLE 6

Expression of Recombinant ORO NP Protein in *E.coli*

Figure 6:
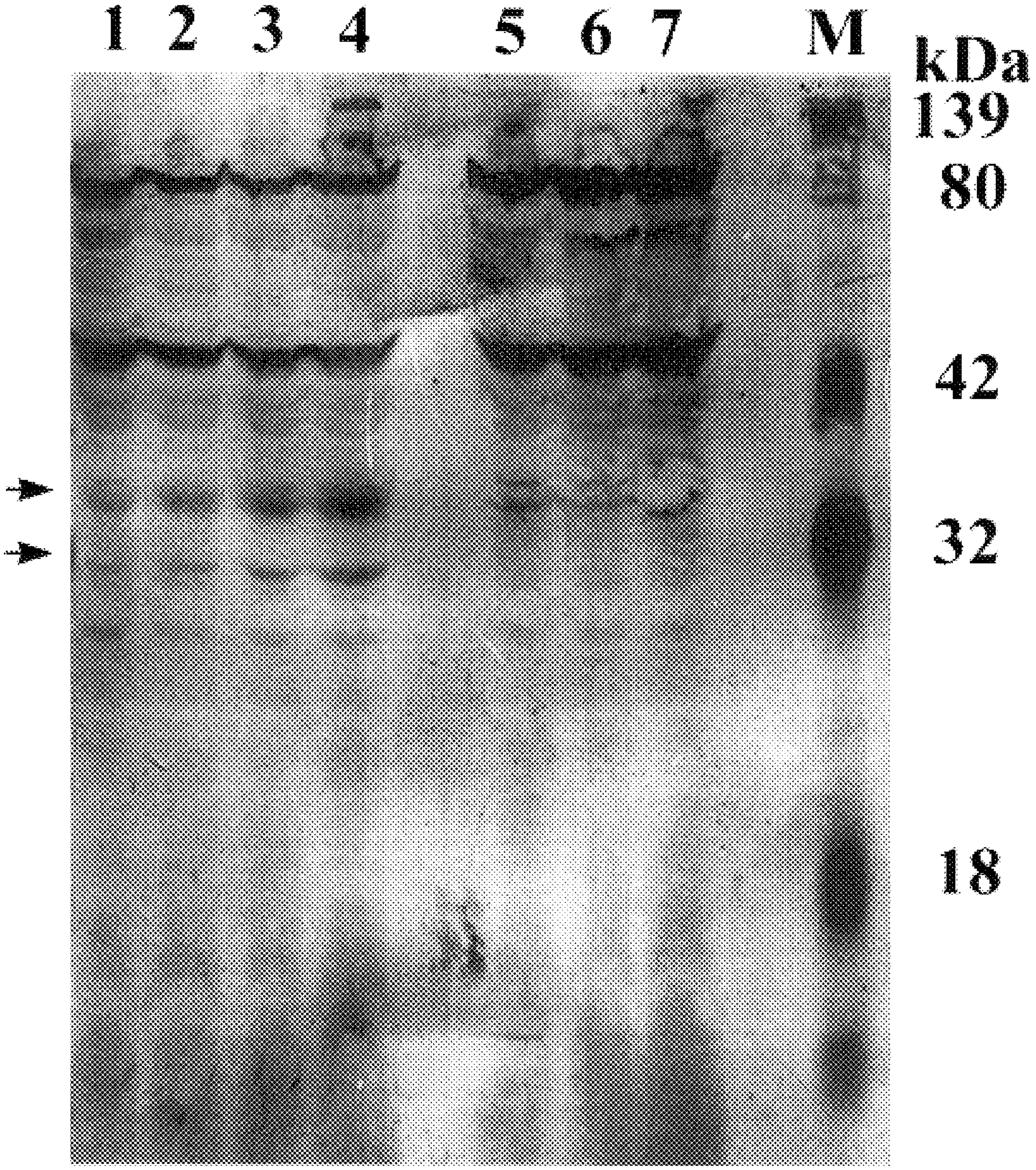
FIG. 6 shows the expression of recombinant protein in *E.coli*. Lanes 1–4: lysate from bacteria containing recombinant plasmid induced for 0, 2, 5 and 9 hours, respectively; Lanes 5–7: lysate from control bacteria induced for 2, 5 and 9 hours, respectively.

Bacteria were grown in LB broth containing ampicillin and protein expression was induced by the addition of 1 mM IPTG for different periods of time. Subsequently, bacterial cells were harvested by centrifugation at 12,000×g for 1 minute and lysed by boiling in SDS-PAGE sample buffer for 5 minutes. The lysate was then centrifuged for 5 minutes at 12,000×g and supernatant was collected. Thereafter, 10 μl of the supernatant was electrophoresed through a 12% SDS-polyacrylamide gel and transferred to a PVDF membrane by electroblotting in Tris-glycine-methanol buffer. The recombinant protein was then detected on the membrane by Western blotting using oropouche-specific mouse antiserum (FIG. 6).

EXAMPLE 7

Sequence Analysis of the Recombinant Plasmid

Figure 8:
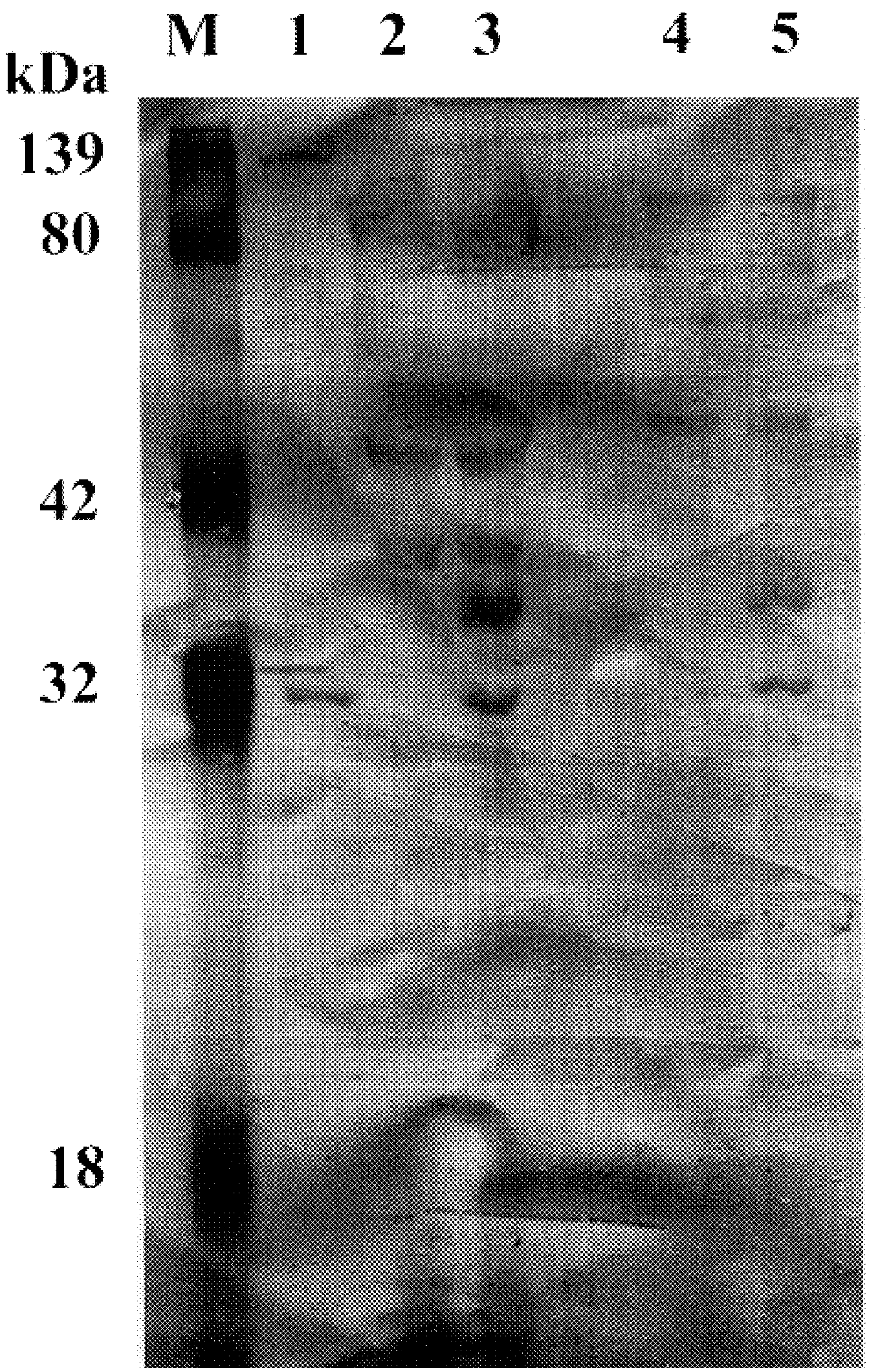
FIG. 8 shows a comparison of the recombinant NP with authentic viral NP protein by Western blotting. Lane 1: cellular extract from oropouche infected vero cells; lanes 2 and 4: lysate from control bacteria; and lanes 3 and 5: lysate from bacteria containing recombinant plasmid. M: molecular weight markers.

To confirm that the NP cDNA has been cloned at the right site and in the right reading frame with respect to the bacterial translation start site, the recombinant plasmid was isolated and its sequence (SEQ ID NOs: 8–9) was determined from upstream to downstream of cloning sites, using the primer 5'-AGAGGTATATATTAATGTATCG-3' (SEQ ID No: 10) which binds 15 nucleotides upstream of bacterial ATG site. The nucleotide sequence of the recombinant plasmid is shown in FIG. 7. A comparison of the recombinant NP with authentic viral NP protein was also studied by Western blotting (FIG. 8).

EXAMPLE 8

Reactivity of the Recombinant Protein to Human Serum

Figure 9:
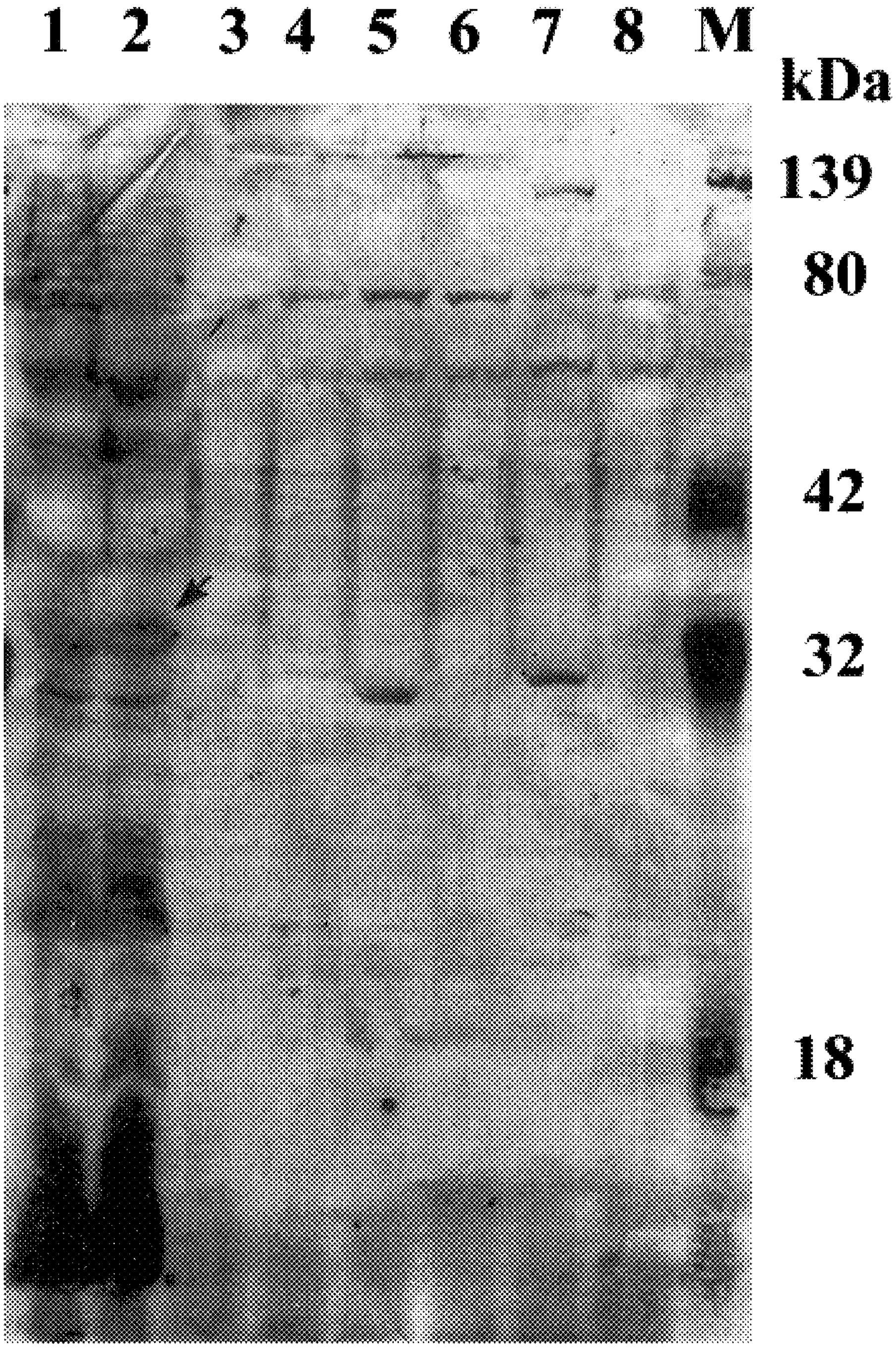
FIG. 9 shows the reactivity of recombinant protein to oropouche-specific human serum. Lane 1: lysate from control bacteria; lane 2: lysate from bacteria expressing recombinant protein; lane 7: lysate from oropouche-infected vero cells.

To determine if the recombinant protein would be recognized by oropouche-specific human serum, lysate from control bacteria, lysate from bacteria expressing recombinant protein, and lysate from oropouche-infected vero cells were analyzed by Western blotting using serum from an individual diagnosed for oropouche fever. The result demonstrates that the recombinant protein was recognized by oropouche-specific human serum. Thus, human anti-oropouche sera recognizes both recombinant NP and viral NP in Western blots (FIG. 9).

Studies were also done to show that the recombinant NP protein cross-reacts with certain antisera raised against bunyaviruses (Table 4). This data shows that mouse anti-sera prepared against different members of the Simbu serogroup recognize the same epitopes on recombinant NP and viral NP with the same specificity indicating that the recombinant NP is antigenically very similar to the viral NP.

TABLE 4

Reactivity of viral NP and recombinant NP to sera raised against other bunyaviruses

| Antiserum against | Viral NP | Recombinant NP |
|---|---|---|
| PARA | + | + |
| SHAMONDA | – | – |
| THIMIRI | + | + |
| MANZANILLA | +/– | – |
| INGWAVUMA | – | – |
| UTINGA | + | + |
| BUTTONWILLOW | – | – |
| SIMBU | + | + |
| SANGO | – | – |
| SABO | – | – |
| SHUNI | + | + |
| SATHUPERI | + | – |
| MERMET | – | – |
| PEATON | – | – |
| AKABANE | + | + |
| DENGUE-1 | ND | – |
| DENGUE-2 | ND | – |
| CATU | ND | – |
| SNOWSHOW HARE | ND | – |

EXAMPLE 9

Purification of Recombinant NP Protein

Figure 10A:
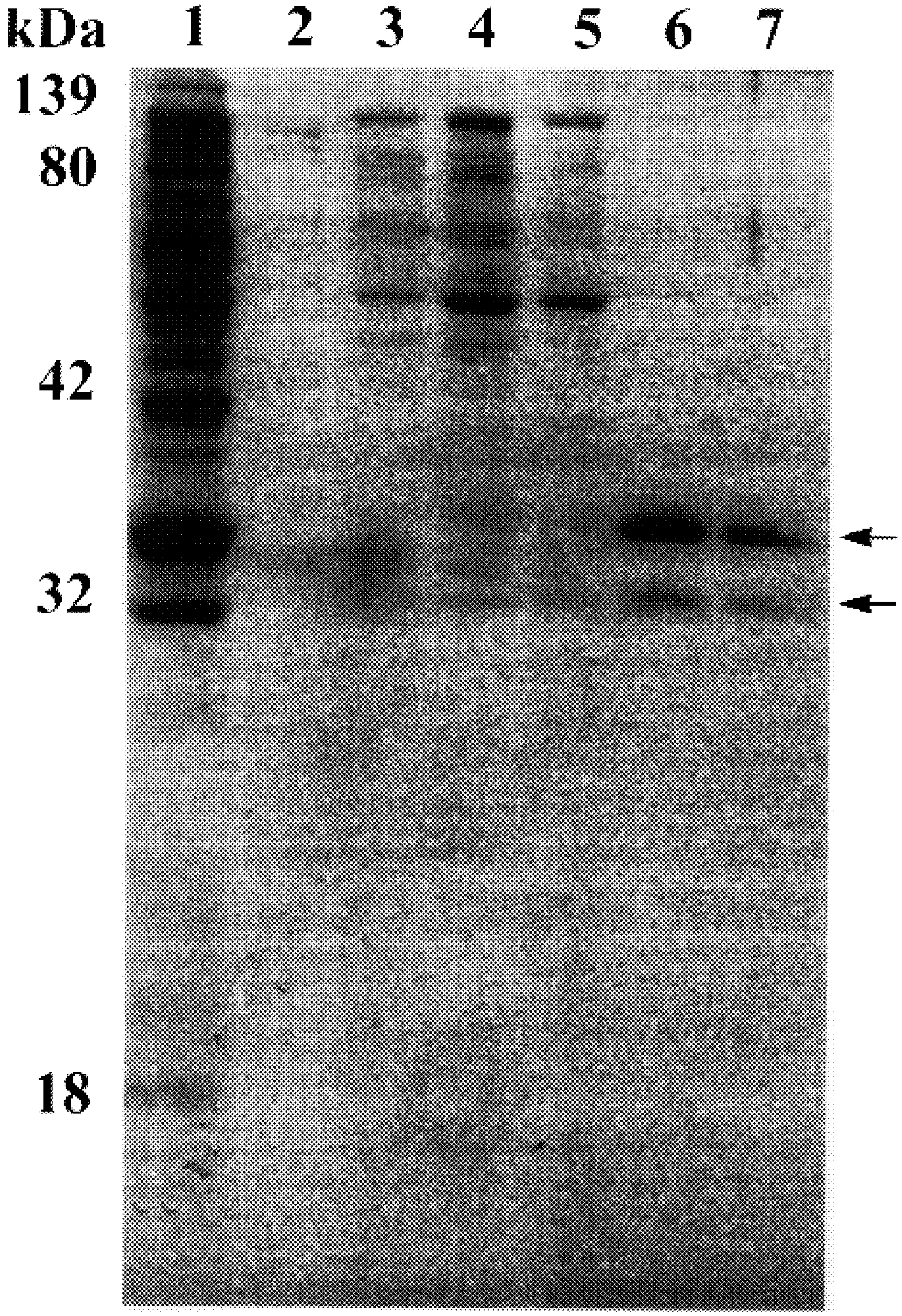
FIGS. 10A–10B show the purification of recombinant NP protein.
Figure 10B:
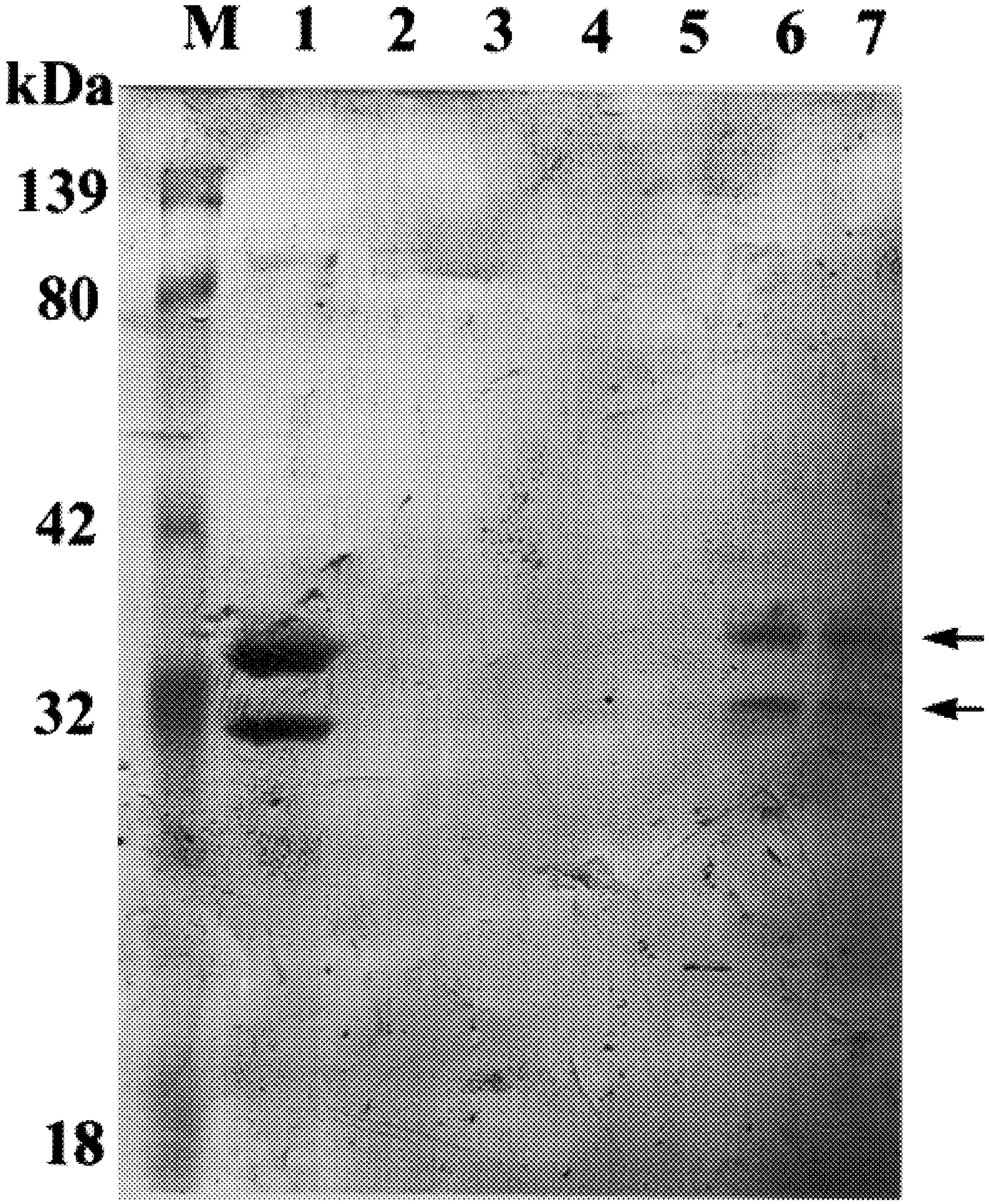

To purify the recombinant protein, bacteria containing the plasmid were grown in LB broth containing ampicillin, induced with 5 mM IPTG for 16–2 hours, harvested by centrifugation and resuspended in sodium-phosphate buffer, pH 7.8. Subsequently, the bacteria were lysed by the addition of lysozyme and alternate cycles of freezing-thawing-sonication. Finally, the lysate was centrifuged at 3,000×g for 15 minutes and supernatant was collected. The supernatant was passed through a column of resin containing bound Ni ions. Thereafter, the column was washed extensively and finally the bound protein was eluted by increasing concentrations of immidazole. Five 1 ml fractions were collected for each immidazole concentration used. For each fraction $A_{280}$ was determined spectrophotometrically and the fractions that showed the presence of protein were analyzed by SDS-polyacrylamide gel electrophoresis followed by coomassie blue staining of the gel (FIG. 10A) and by Western blotting using oropouche-specific mouse antiserum (FIG. 10B). The data demonstrate that the recombinant NP protein can be purified.

To demonstrate that purified recombinant NP evokes a protective immune response, mice are immunized with recombinant NP by the subcutaneous route and challenged three weeks later with a lethal dose of Oropouche virus by the intracerebral route. Protection was analyzed in terms of survival of mice following challenge and increased average survival time of NP-immunized mice versus mock-infected controls.

EXAMPLE 10

ELISA

The methodology for the use of an ELISA assay in the present invention is basically as follows. Wells of a flat bottom 96 well microtiter plate are coated with the purified recombinant protein diluted in carbonate-bicarbonate buffer (pH 9.6) and the plate is incubated at 4° C. for 12–16 hours. The wells are then washed 5–10 times with wash buffer (PBS containing 0.05% Tween-20, 1 mM EDTA, 0.25% BSA) in an automatic ELISA washer, followed by the addition of 20 $\mu$l blocking buffer (1% horse serum in PBS) and incubation at 37° C. for 15 minutes. Each well of the plate containing the recombinant antigen is then added with 100 $\mu$l of appropriately diluted primary antibody (ORO specific mouse antibodies or patient's sera) and the plate is then incubated at 37° C. for 1 hour. After the incubation, the plate is again washed as above, followed by the addition of 100 $\mu$l appropriately diluted secondary antibody (horseradish peroxidase conjugated anti-mouse IgG or anti-human IgG) and the plate is again incubated at 37° C. for 1 hour. Thereafter, the wells are washed as above and 100 $\mu$l of horseradish peroxidase substrate (2.2'-azino-di{3-ethyl-benzthiazoline sulfonate}) is added to each well and the place is incubated at room temperature until a blue green color develops to a maximum intensity. The reaction is then stopped by the addition of 100 $\mu$l 1% SDS and the intensity of the color in each well is recorded by taking $OD_{405}$ in an ELISA reader. After correcting for background absorbance, the values are plotted using sigma plot software.

Figure 12:
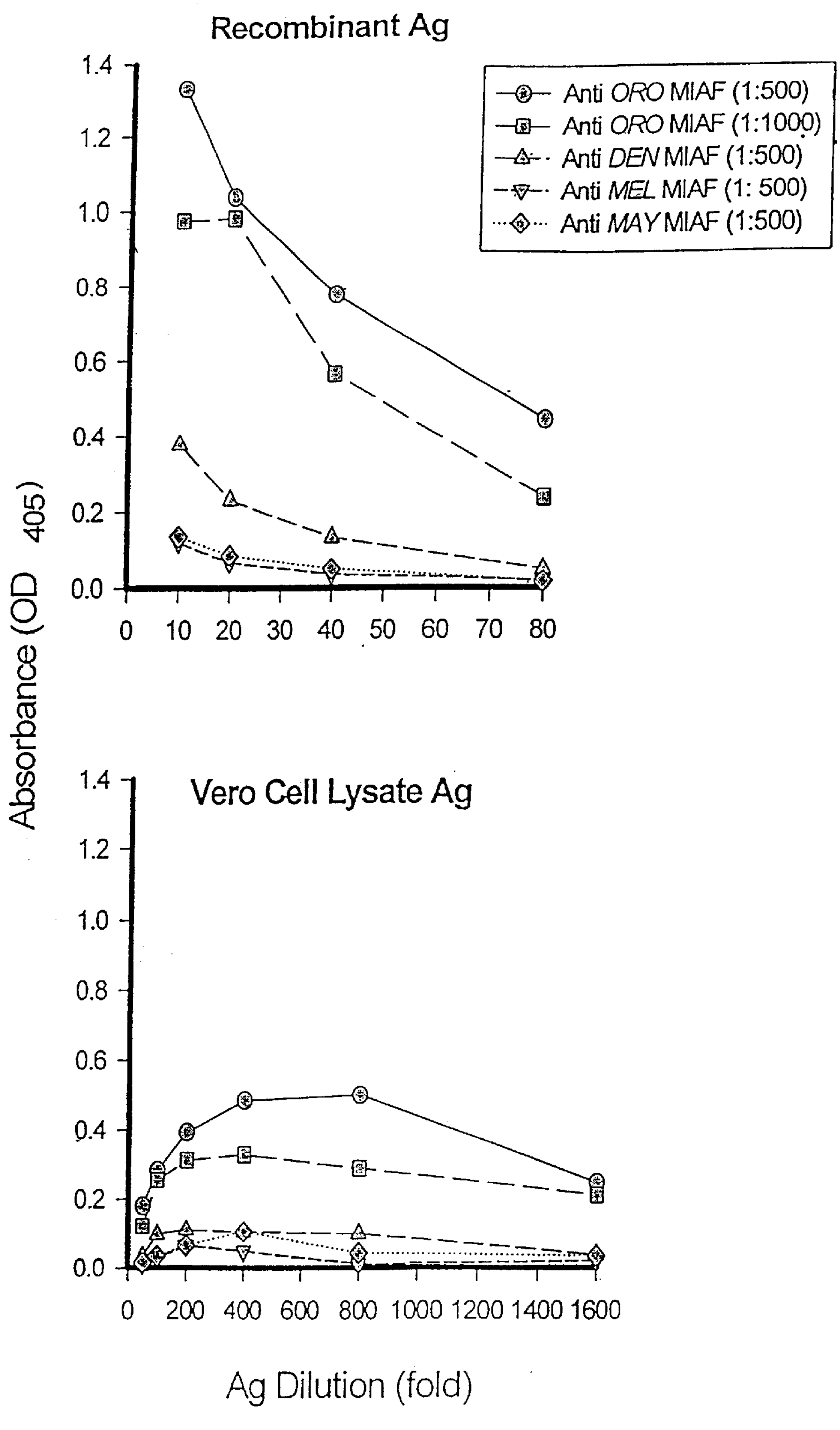
FIG. 12 shows comparison between recombinant oropouche N protein and infected-Vero cell lysate antigen using IgG ELISA. Top panel: Recombinant oropouche NP; bottom panel: Infected-Vero cell lysate antigen.

Specifically, IgG ELISA was used for comparing between recombinant oropouche N protein and oropouche infected-Vero cell lysate antigen (Watts et al. Am. J. Trop. Med. Hyg 56: 148–152, 1997). Wells of an ELISA plate were coated with various dilutions of each antigen followed by incubation with primary antibody (anti-ORO, anti-Dengue, anti-Mayaro, or anti-Melao MIAF). Subsequently, the plate was washed and secondary antibody (peroxidase conjugated goat-antimouse IgG) was added to each well. After incubation for 1 hour, the plate was washed and finally substrate was added to each well. Absorbance was measured at 405 nm wavelength in a spectrophotometer. Results were plotted after subtracting the background (absorbance in the blank well, FIG. 12). The data shows that the recombinant oropouche N protein ELISA was more specific than the Peruvian ELISA.

Figure 13:
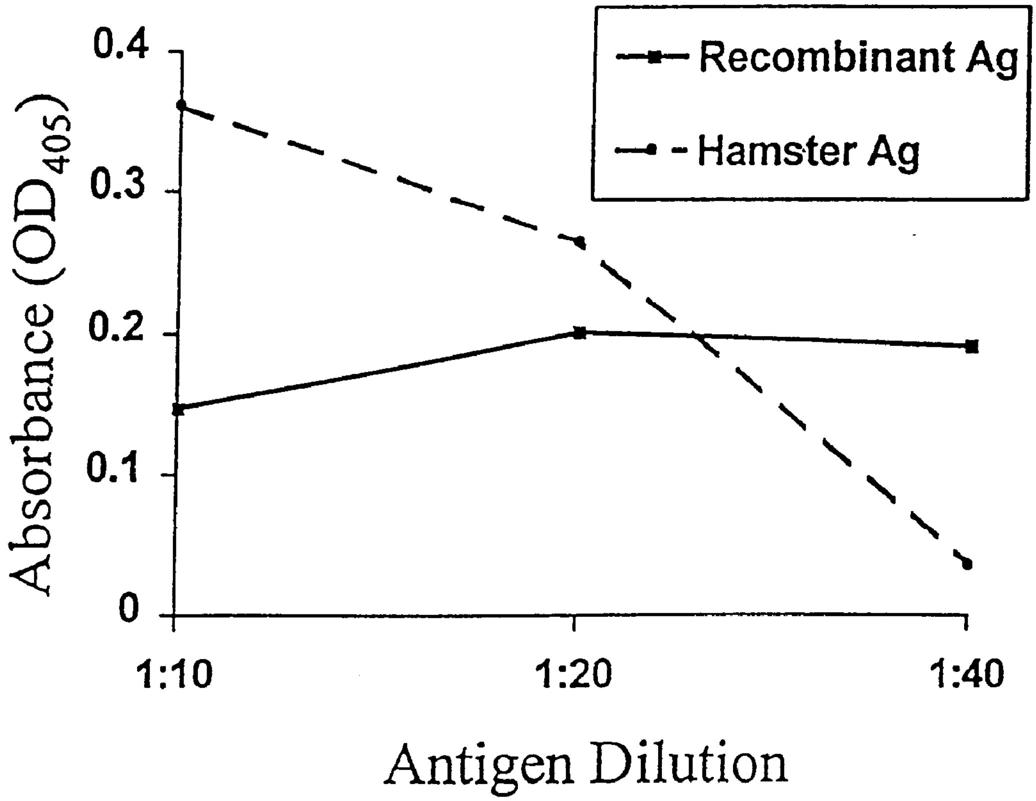
FIG. 13 shows comparison between recombinant oropouche N protein (rORO NP) r antigen and infected hamster antigen using IgM capture ELISA.

IgM capture ELISA was used for comparing between recombinant oropouche N protein (rORO NP) r antigen. Wells of a n ELISA plate were coated with anti-human IgM and human sera from oropouche-infected or uninfected individuals were added to the respective wells. The plate was then incubated followed by the addition of various dilutions of antigen (rORO NP or hamster antigen). After 1 hour, the plate was washed and anti-oropouche MIAF was added to each well. Subsequently, the plate was washed and conjugate (peroxidase-conjugated goat anti-mouse IgG) was added to each followed by washing and addition of the substrate. Absorbance was measured at 405 nm wavelength in a spectrophotometer. Results were plotted after subtracting the background (absorbance in the blank well, FIG. 13). The data shows that although lower dilutions of hamster antigen gave higher absorbance than the recombinant oropouche ELISA, the hamster ELISA rapidly loss reactivity on dilution of hamster antigen whereas the recombinant oropouche N protein ELISA had higher specificity on dilution of the recombinant antigen.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. Isolated and purified Oropouche NP protein encoded by DNA selected from the group consisting of:

(a) isolated DNA having a sequence of SEQ TD) No. 3 and which encodes a Oropouche NP protein;

(b) isolated DNA which is 90% or more homologous to isolated DNA of (a) above and which encodes a Oropouche NP protein; and (c) isolated DNA differing from the isolated DNAs of (a) and (b) above in codon sequence due to the degeneracy of the genetic code, and which encodes a Oropouche NP protein.

2. The isolated and purified Oropouche NP protein of claim 1 having the amino acid sequence shown in SEQ ID No. 11.

3. A kit for the immunodetection of Oropouche virus, said kit containing:

(a) recombinant Oropouche NP protein;

(b) anti-Oropouche antibodies; and (c) a secondary antibody conjugated to a molecule useful for detection purposes.

* * * * *

SEQUENCE LISTING

```
<160> NUMBER OF SEQ ID NOS:  12

<210> SEQ ID NO 1
<211> LENGTH: 18
<212> TYPE: DNA
<213> ORGANISM: artificial sequence
<220> FEATURE:
<221> NAME/KEY: primer_bind
<223> OTHER INFORMATION: Sense primer used for RT-PCR of S RNA cDNA

<400> SEQUENCE: 1

agtagtgtac tccactat                                                    18


<210> SEQ ID NO 2
<211> LENGTH: 18
<212> TYPE: DNA
<213> ORGANISM: artificial sequence
<220> FEATURE:
<221> NAME/KEY: primer_bind
<223> OTHER INFORMATION: Antisense primer used for PCR of S RNA cDNA

<400> SEQUENCE: 2

agtagtgtgg ctccacat                                                    18


<210> SEQ ID NO 3
<211> LENGTH: 754
<212> TYPE: DNA
<213> ORGANISM: artificial sequence
<220> FEATURE:
<223> OTHER INFORMATION: Nucleotide sequence of sense strand of S RNA
      cDNA

<400> SEQUENCE: 3

agtagtgtac tccactattc aaaacataaa aagaaattcc aataatgtca gagttcattt      60

tcaacgatgt accagcccgg actacatcta catttgatcc ggaagcagca tatgtggcat     120

ttgaagctag atacggacaa gtgctcaatg ctggtgttct tagagtcttc ttcctcaacc     180

aaaagaaggc caaagatgtc ttacgtaaga catcgaggcc catggttgac cttacttttg     240

gtggggtcca atttgcaatg gttaataacc atttcccaca gttccaatcg aatccagtgc     300

cggacaacgg tcttaccttg caccgtctgt caggatacct agcgcgctgg gcctttactc     360

agatgcgatc accaattaag caagctgagt tcagagctac tgtagtagtg cctttggctg     420

aggtaaaagg ctgtacttgg aatgatggtg atgcaatgta cctggggttt gctgctggtg     480

ctgagatgtt cctgcagacg ttcactttct tccctttggt gattgagatg catagggttc     540

tcaaggatgg catggatgtc aactttatga agaaagtcct ccggcaacgg tatggccaaa     600
```

-continued aaactgccga gcaatggatg cgtgaagaaa tagttgctgt aagagcagct tttgaagctg 660
taggcactct ggcctgggcc agaactggat tctccccagc agcaagagac ttcttgcgcc 720
aattcggaat tggcatatag tggagtacac tact 754

<210> SEQ ID NO 4
<211> LENGTH: 36
<212> TYPE: DNA
<213> ORGANISM: artificial sequence
<220> FEATURE:
<221> NAME/KEY: primer_bind
<223> OTHER INFORMATION: Nucleotide sequence of oropoucheN5 upstream primer

<400> SEQUENCE: 4
aaatgaacac tgacattatt ggaatttctt tttatg 36

<210> SEQ ID NO 5
<211> LENGTH: 31
<212> TYPE: DNA
<213> ORGANISM: artificial sequence
<220> FEATURE:
<221> NAME/KEY: primer_bind
<223> OTHER INFORMATION: Nucleotide sequence of oropoucheN5 upstream primer

<400> SEQUENCE: 5
aaagaggatc caataatgtc agagttcatt t 31

<210> SEQ ID NO 6
<211> LENGTH: 30
<212> TYPE: DNA
<213> ORGANISM: artificial sequence
<220> FEATURE:
<221> NAME/KEY: primer_bind
<223> OTHER INFORMATION: Nucleotide sequence of oropoucheN3 downstream primer

<400> SEQUENCE: 6
gtgaattcca ctatatgcca attccgaatt 30

<210> SEQ ID NO 7
<211> LENGTH: 36
<212> TYPE: DNA
<213> ORGANISM: artificial sequence
<220> FEATURE:
<221> NAME/KEY: primer_bind
<223> OTHER INFORMATION: Nucleotide sequence of oropoucheN3 downstream primer

<400> SEQUENCE: 7
ccaattcgga attggcatat agtggagtac actact 36

<210> SEQ ID NO 8
<211> LENGTH: 179
<212> TYPE: DNA
<213> ORGANISM: artificial sequence
<220> FEATURE:
<223> OTHER INFORMATION: Nucleotide sequence of recombinant plasmid

<400> SEQUENCE: 8
ataaataagg gagttaaaca tggggggttc tcatcatcat catcatcatg gtatggctag 60
catgactggt ggacagcaaa tgggtcggga tctgtacgac gatgacgata aggatccaat 120
aatgtcagag ttcattttca atgatgtacc acaacggact acatctacat ttgatccgg 179

-continued

```
<210> SEQ ID NO 9
<211> LENGTH: 58
<212> TYPE: PRT
<213> ORGANISM: artificial sequence
<220> FEATURE:
<223> OTHER INFORMATION: Amino acid sequence encoded by recombinant
      plasmid cDNA

<400> SEQUENCE: 9

Ile Arg Glu Leu Asn Met Gly Gly Ser His His His His His His
                5                   10                  15

Gly Met Ala Ser Met Thr Gly Gly Gln Gln Met Gly Arg Asp Leu
                20                  25                  30

Tyr Asp Asp Asp Asp Lys Asp Pro Ile Met Ser Glu Phe Ile Phe
                35                  40                  45

Asn Asp Val Pro Gln Arg Thr Thr Ser Thr Phe Asp Pro
                50                  55


<210> SEQ ID NO 10
<211> LENGTH: 22
<212> TYPE: DNA
<213> ORGANISM: artificial sequence
<220> FEATURE:
<221> NAME/KEY: primer_bind
<223> OTHER INFORMATION: Primer which binds 15 nucleotides upstream of
      bacterial ATG site used to amplify recombinant
      plasmid cDNA

<400> SEQUENCE: 10

agaggtatat attaatgtat cg                                              22


<210> SEQ ID NO 11
<211> LENGTH: 231
<212> TYPE: PRT
<213> ORGANISM: Bunyavirus
<220> FEATURE:
<222> LOCATION: 46..736
<223> OTHER INFORMATION: Deduced amino acid sequence of Oropouche Np
      protein

<400> SEQUENCE: 11

Met Ser Glu Phe Ile Phe Asn Asp Val Pro Gln Arg Thr Thr Ser
                5                   10                  15

Thr Phe Asp Pro Glu Ala Ala Tyr Val Ala Phe Glu Ala Arg Tyr
                20                  25                  30

Gly Gln Val Leu Asn Ala Gly Val Val Arg Val Phe Phe Leu Asn
                35                  40                  45

Gln Lys Lys Ala Lys Asp Val Leu Arg Lys Thr Ser Arg Pro Met
                50                  55                  60

Val Asp Leu Thr Phe Gly Gly Val Gln Phe Ala Met Val Asn Asn
                65                  70                  75

His Phe Pro Gln Phe Gln Ser Asn Pro Val Pro Asp Asn Gly Leu
                80                  85                  90

Thr Leu His Arg Leu Ser Gly Tyr Leu Ala Arg Trp Ala Phe Thr
                95                  100                 105

Gln Met Arg Ser Pro Ile Lys Gln Ala Glu Phe Arg Ala Thr Val
                110                 115                 120

Val Val Pro Leu Ala Glu Val Lys Gly Cys Thr Trp Asn Asp Gly
                125                 130                 135

Asp Ala Met Tyr Leu Gly Phe Ala Ala Gly Ala Glu Met Phe Leu
                140                 145                 150
```

-continued

```
Gln Thr Phe Thr Phe Phe Pro Leu Val Ile Glu Met His Arg Val
                155                 160                 165

Leu Lys Asp Gly Met Asp Val Asn Phe Met Lys Lys Val Leu Arg
                170                 175                 180

Gln Arg Tyr Gly Gln Lys Thr Ala Glu Gln Trp Met Arg Glu Glu
                185                 190                 195

Ile Val Ala Val Arg Ala Ala Phe Glu Ala Val Gly Thr Leu Ala
                200                 205                 210

Trp Ala Arg Thr Gly Phe Ser Pro Ala Ala Arg Asp Phe Leu Arg
                215                 220                 225

Gln Phe Gly Ile Gly Ile
                230


<210> SEQ ID NO 12
<211> LENGTH: 91
<212> TYPE: PRT
<213> ORGANISM: Bunyavirus
<220> FEATURE:
<222> LOCATION: 68..338
<223> OTHER INFORMATION: Deduced amino acid sequence of Oropouche NSs
      protein

<400> SEQUENCE: 12

Met Tyr His Asn Gly Leu His Leu His Leu Ile Arg Lys Gln His
                5                   10                  15

Met Trp His Leu Lys Leu Asp Thr Asp Lys Cys Ser Met Leu Val
                20                  25                  30

Leu Leu Glu Ser Ser Ser Ser Thr Lys Arg Arg Pro Lys Met Ser
                35                  40                  45

Tyr Val Arg His Arg Gly Pro Trp Leu Thr Leu Leu Leu Val Gly
                50                  55                  60

Ser Asn Leu Gln Trp Leu Ile Thr Ile Ser His Ser Ser Asn Arg
                65                  70                  75

Ile Gln Cys Arg Thr Thr Val Leu Pro Cys Thr Val Cys Gln Asp
                80                  85                  90

Thr
```